United States Patent [19]

Berman et al.

[11] 3,946,739
[45] Mar. 30, 1976

[54] SELF-CONTAINED VACUUM ASPIRATOR

[75] Inventors: Richard M. Berman, Dresher, Pa.;
Bernard Schwartz, Springfield, N.J.

[73] Assignee: Alphamedics Mfg. Co., Levittown, Pa.

[22] Filed: June 30, 1975

[21] Appl. No.: 591,507

Related U.S. Application Data

[62] Division of Ser. No. 399,535, Sept. 21, 1973.

[52] U.S. Cl. ............................. 128/304; 128/276
[51] Int. Cl.² ................... A61B 17/22; A61M 1/00
[58] Field of Search ........................... 128/276, 304

[56] References Cited
UNITED STATES PATENTS

| | | | |
|---|---|---|---|
| 2,913,220 | 11/1959 | Cover | 251/327 X |
| 2,986,367 | 5/1961 | Le Rouax | 251/327 X |
| 3,542,031 | 11/1970 | Taylor | 128/276 X |
| 3,833,000 | 9/1974 | Bridgman | 128/276 |
| 3,863,624 | 2/1975 | Gram | 128/276 X |
| 3,889,682 | 6/1975 | Denis | 128/276 X |

Primary Examiner—Channing L. Pace
Attorney, Agent, or Firm—Lerner, David, Littenberg & Samuel

[57] ABSTRACT

A self-contained vacuum aspirator system is disclosed which comprises a container having a vacuum applied therein; a valve assembly secured to said container for selectively allowing the passage of fluid into said container; a curette in communication with an aperture in said valve assembly; and an air permeable collection means supported within said container by the aforementioned valve assembly in communication with an opening in said valve assembly for accumulating matter collected by said curette when the valve assembly is operating to establish communication between the aforementioned aperture and opening. The valve assembly includes a first member having the aforementioned aperture therethrough with the first member having a first surface on which is positioned first sealing means surrounding said aperture and second sealing means surrounding said first sealing means; and a second member secured to said first member with the second member having the aforementioned opening therethrough and a first surface on which is positioned third sealing means surrounding said opening and fourth sealing means surrounding said third sealing means; and a slide member having a passageway therethrough with the slide member being moveably mounted between said first surfaces of the first and second members and sealingly engaged on opposite sides thereof by the first, second, third and fourth sealing means, with the slide member being moveable between a first position which interrupts communication between a first position which interrupts communication between said aperture and said opening and a second position in which the passageway through the slide member establishes communication between the aperture in the first member and the opening in the second member to permit flow through the valve assembly.

3 Claims, 8 Drawing Figures

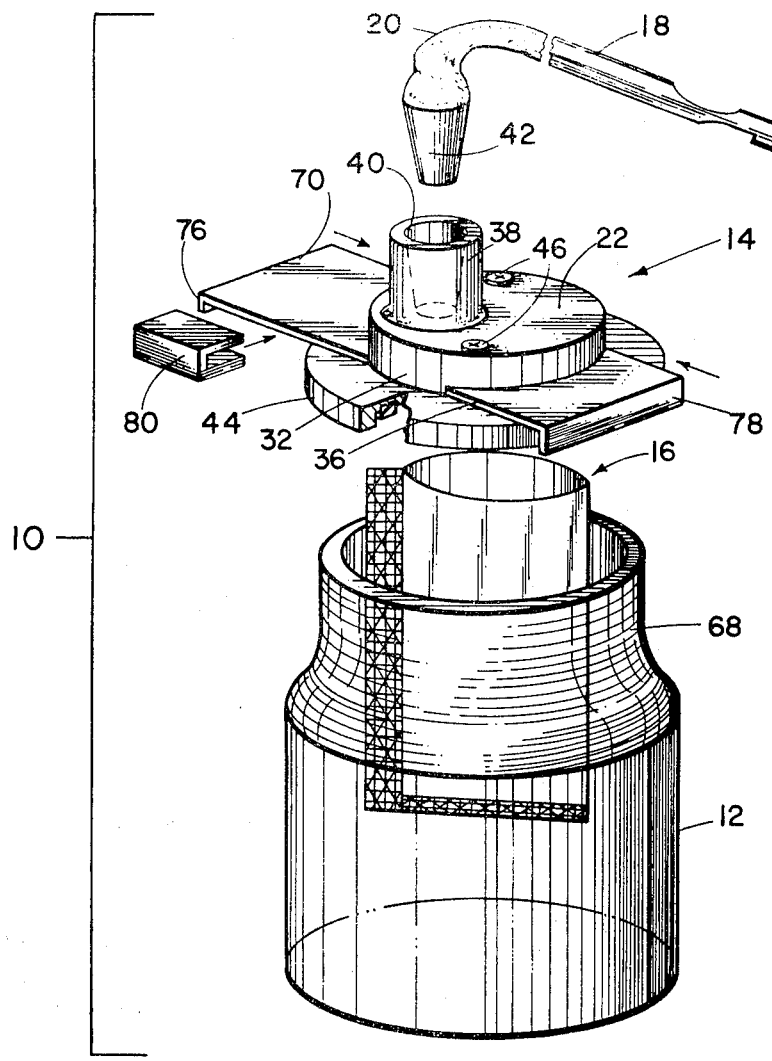
FIG. 1
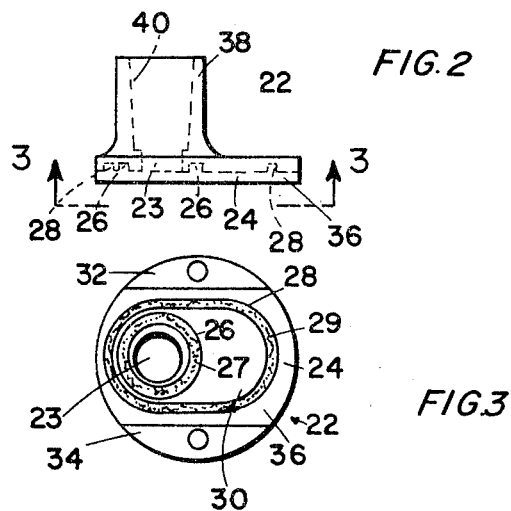
FIG. 2
FIG. 3

SELF-CONTAINED VACUUM ASPIRATOR

This is a division of application Ser. No. 399,535, filed Sept. 21, 1973.

FIELD OF THE INVENTION

This invention relates to a self-contained vacuum aspirator system and in addition to an improved valve assembly utilized in such system.

BACKGROUND OF THE INVENTION

Vacuum curettage has received recent and extensive attention in the art as an improved means for pregnancy termination, endometrial biopsy, menstrual regulation, spontaneous incomplete abortion, and outpatient or office curettage, as well as other conditions. The vacuum procedure promises advantages over the conventional sharp curettage procedure in that more effective evacuation is obtained in a shorter time and with a lesser loss of blood. The art has come to recognize that there is a lesser likelihood of residual material remaining in the uterus after vacuum curettage than with sharp curettage.

In vacuum curettage, an elongated tube is used in which an aspiration inlet is provided at the front or proximal end, and to which a connecting vacuum end is joined to the rear or distal end. The normal procedure provides for dilating the cervix of the uterus to a size greater than the tube or curette so that the curette may be introduced into the uterus to the full depth of the endometrial cavity. The practitioner moves the front end of the curette over the surface of the uterus and suction induces the fetal or gestational tissue, or other biological material, through the aspiration inlet. This tissue is usually passed out of the curette into a communicating vacuum trap or container. A prior art vacuum curette system is disclosed, for example, in U.S. Pat. No. 3,542,031, in which a vacuum source is applied to a container to withdraw tissue collected by the curette through a stopper and into a tissue collection chamber. It will be appreciated, however, that the prior art as exemplified by the aforementioned U.S. Pat. No. 3,542,031, has inherent drawbacks which to a great extent limit its application.

For example, the system of the aforenoted patent requires the practitioner to have a vacuum pump at his disposal when employing the curette system described therein. Not only is this a relatively expensive item, but its operation requires addtional specialized knowledge not necessarily possessed by the relatively large number of practitioners who are now employing such systems as a result of recent changes in the law with regard to the performance of abortions.

SUMMARY OF THE INVENTION

In contradistinction to the prior art, the instant invention provides for a self-contained vacuum aspirator system which employs a prepackaged container having a vacuum applied therein and a curette associated therewith by means of which a vacuum curettage abortion can be simply and easily effectuated without the need for a separate vacuum source. In furtherance of this broad aspect of the invention, a novel valve assembly is provided through which a vacuum can be applied in the factory to the container and thereafter the valve assembly operated to maintain the vacuum in the container. When it is desired to perform the abortion, the curette is introduced into the uterus and the valve assembly is operated so as to communicate the curette with the vacuum in the container to thereby draw the tissue collected by the curette into an air permeable collection trap supported within the container. Thereafter, the valve assembly may be removed from the container and the entire subassembly, including the curette and the valve assembly, disposed of.

OBJECTS OF THE INVENTION

Accordingly, it is an object of the instant invention to provide a self-contained vacuum aspirator system by which a vacuum curettage procedure may be performed without the necessity of a supplemental vacuum source.

Another object of the instant invention is to provide such a prepackaged vacuum aspirator system in which a vacuum can be applied during manufacture and, thereafter, the system stored at the physician's office until the operation is performed.

Still another object of the instant invention is to provide such a system which includes a novel valve assembly for maintaining a vacuum which has been preapplied to the container therof, thereby greatly increasing the "shelf life" of the entire system.

BRIEF DESCRIPTION OF THE SEVERAL VIEWS OF THE DRAWINGS

FIG. 1 is an exploded perspective view of the self-contained vacuum aspirator system of the instant invention.

FIG. 2 is a side elevational view of a portion of the valve assembly shown in FIG. 1.

FIG. 3 is a bottom view of the element shown in FIG. 2 taken along the arrows 3—3 thereof.

DETAILED DESCRIPTION OF THE INVENTION

Figure 4:
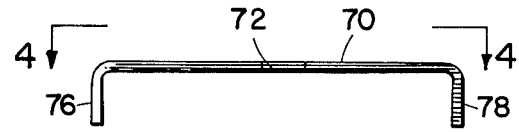
FIG. 4 is a side elevational view of another portion of the valve assembly shown in FIG. 1.

Turning to the Figures, wherein like numerals represent like elements, there is shown in FIG. 1 the self-contained vacuum aspirator system 10 of the instant invention. Broadly speaking, the system includes a container 12, which is preferably a glass jar, a valve assembly broadly designated 14, a collection trap 16 supported by the valve assembly 14 within the container 12, and a conventional curette 18 connected by appropriate tubing 20 to the valve assembly 14 as will be described in greater detail.

The valve assembly 14 comprises a first member 22 (FIGS. 2 and 3) having an aperture 23 therethrough. An undersurface 24 of the first member 22 includes a circular recess 26 which carries a circular O-ring sealing member 27 therein and a second generally oval recess 28 carrying a generally oval O-ring like sealing member 29 therein. It will be seen from FIG. 3, that the circular O-ring 27 immediately surrounds the aperture 23 while the oval O-ring like member 29, which is actually a circular O-ring placed in an oval recess, is relatively substantially larger than the circular O-ring 27 so as to provide a space 30 on the undersurface 24 which lies within the confine established by the inner and outer O-ring like members 27 and 29, respectively.

For purposes to be further described, the first member 22 further includes depending side portions 32 and 34 which establish a guide channel 36 therebetween. The first member 22 further includes an integrally upstanding cylindrical receptacle 38 which includes an internally tapered passage 40 in communication with the aperture 23. As suggested in FIG. 1, the passage 40 resides in a press-fit fashion in the externally tapered terminating portion 42 of the curette 18.

Figure 6:
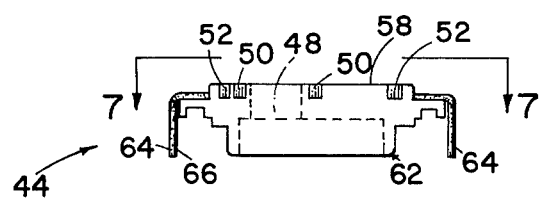
FIG. 6 is a side elevational view of another portion of the valve assembly shown in FIG. 1.
Figure 7:
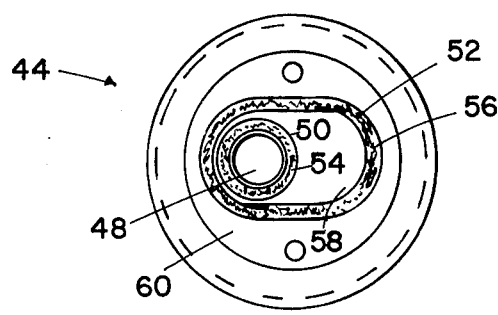
FIG. 7 is a planned view of the element shown in FIG. 6 taken along the arrows 7—7 thereof.

As best seen in FIGS. 6 and 7, the valve assembly 14 further comprises a second member 44 which may be removably secured with respect to the first member 22 by means of fasteners 46 (FIG. 1) which pass through the depending guide portions 32 of the first member 22 into engagement with the second member 44. The second member 44 includes an opening 48 having a circular recess 50 disposed thereabout and a generally oval recess 52 located about the inner recess 50. As best seen in FIG. 7, the circular recess 50 receives a circular O-ring sealing member 54 while the oval recess 52 receives an oval O-ring like sealing member 56 which is actually a circular O-ring placed in an oval recess. As was the case for the sealing member 27 and 29 for the first member 22, the sealing member 56 is substantially larger than the sealing member 54 to define a portion 58 of the top surface 60 of the second member 44 which is confined by portions of the sealing members 54 and 56.

The undersurface of the second member 44 further includes an integrally depending cylindrical embossment 62 which is in communication with the opening 48. In accordance with this aspect of the invention, the collection trap 16, preferably an air permeable woven plastic bag-like element or a plastic vial, has a diameter approximately the same as the diameter of the embossment 62 whereby the collection trap 16 can be telescopically urged onto the embossment 62 for a frictional press fit therebetween.

The second member 44 is further provided with an annular downturned flange portion 64 by which the entire valve assembly 14 can be removably secured to the container 12, for example, by being provided with internal threads 66 which may be received on an externally threaded neck portion 68 of the container 12.

Figure 5:
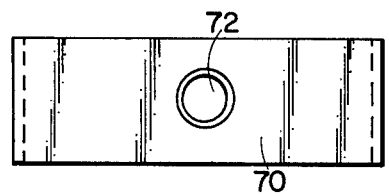
FIG. 5 is a planned view of the member shown in FIG. 4 taken along the arrows 4—4 thereof.

Slideably mounted within the channel 36 established between the depending guide portions 32 and 34 of the first member 22 is a slide member 70 (FIGS. 4 and 5) having a passageway 72 therethrough. As thus established, the slide member 70 is "sandwiched" between the undersurface 24 of the first member 22 and the upper surface 60 of the second member 44 and is sealingly engaged on opposite sides thereof by the O-ring like sealing members 27, 29 and 54, 56 (see FIG. 8).

Figure 8:
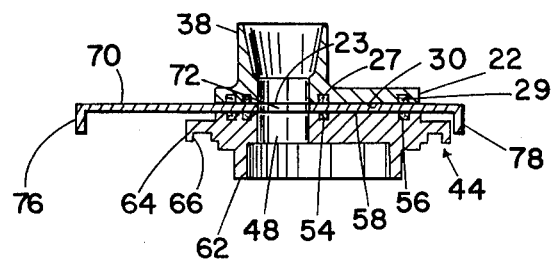
FIG. 8 is a side view of the assembled valve assembly comprising the elements shown in FIGS. 2 through 7.

The slide member 70 may be moved between a first position which interrupts fluid communication between aperture 23 in first member 22 and the opening 48 in the second member 44 and a second position illustrated in FIG. 8 in which the passageway 72 establishes an unobstructed communication between aperture 23 and opening 48. It will be appreciated that when the slide member 70 is in its first blocking position, the slide member 70 would be moved to the right as viewed in FIG. 8, such that the passageway 72 would be situated between the confronting intermediate portions 30 and 58 of the surfaces 24 and 60, respectively, which are defined between the O-ring sealing members 27 and 29 on the first member 22 and the O-ring sealing members 54 and 56 on the second member 44. Thus, even when the slide member 70 is in its blocking position, the passageway 72 therethrough will be sealingly retained within a sealed enclosure. As will be described below, this is a particularly important aspect of the valve assembly 14 since it prevents the loss of vacuum in the jar 12 when the system is "on the shelf" in a physician's office.

To uniquely establish the aforenoted first and second positions for the slide member 70, limit stops in the forms of depending flanges 76 and 78 are provided at opposite ends of the slide member 70. Thus, if the operator slides the slide member 70 all the way to the left in FIG. 8 such that the depending flange 78 confronts the second member 44, the passageway 72 will be properly established in alignment with the aperture 23 and the opening 48 in the first member 22 and second member 44, respectively. When the operator slides the slide member 70 all the way to the right, as viewed in FIG. 8, such that the depending flange 76 confronts the second member 44, the passageway 72 will properly be located within the confines of the sealing members 27, 29 and 54, 56, as described above. As best seen in FIG. 1, a removable U-shaped channel member 80 may be frictionally secured on the slide member 70 to prevent accidental displacement of the slide member 70 from the first blocking position to the second communicating position.

In employing the system of the instant invention, the valve assembly 14 is secured to the container 12 and the slide member 70 moved to its second position in which the passageway 72 establishes communication between the aperture 23 and the opening 48. At this time, and perferably at the site of manufacture, a vacuum is applied through the aperture 23 to evacuate the container 12. When the proper vacuum has been achieved, the slide member 70 is slid to its blocking position and the U-shaped channel member 80 slid onto the slide member 70 to prevent accidental displacement of the slide member. It will be appreciated that the vacuum will be held in the jar 12 by virtue of the fact that the passageway 72 in the slide member 70 is retained as aforedescribed, within the confines of the sealing members 27, 29 and 54, 56. The completely self-contained aspirator system may now be shipped to the physician or hospital and stored on the shelf.

When it is desired to perform aspiration procedure, the end portion 42 of the curette 18 is press-fitted into the cylindrical receptacle 38 (or it could be assembled in this condition at the factory), the curette is introduced into the uterus, and, thereafter, the slide member 70 is moved to its second position in which the passageway 72 establishes unobstructed communication between the aperture 23 and the opening 48. The prepackaged vacuum in the jar 12 will induce a suction at the tip of the curette 18, thereby inducing the fetal or gestational tissue or other biological material through the aspiration inlet thereof, through the valve assembly 14 and into the collection trap 16. When the operation is completed, the entire assembly may be used as a shipping container for sending the biological material to the pathology laboratory or the curette, valve assembly 14, and trap 16 may be completely disposed of and, for that matter, jar 12 can be disposed of if desired. Alternatively, the jar 12 and valve assembly 14 can be washed, sterilized and recycled by the manufacturer. It will be appreciated that the parts of the valve assembly 14 are manufactured of relatively inexpensive materials, thereby economically warranting their disposal.

Although this invention has been described with respect to its preferred embodiments, it should be understood that many variations and modifications will now be obvious to those skilled in the art, and it is preferred, therefore, that the scope of the invention be limited, not by the specific disclosure herein, only by the appended claims.

What is claimed is:

1. A self-contained vacuum aspirator system comprising
a container having a vacuum applied therein;
a valve assembly secured to said container for selectively allowing the passage of fluid into said container; said valve assembly comprising
a first member having an aperture therethrough, said first member having a first surface on which is positioned first sealing means surrounding said aperture and second sealing means surrounding said first sealing means;
a second member secured to said first member, said second member having an opening therethrough and a first surface on which is positioned third sealing means surrounding said opening and fourth sealing means surrounding said third sealing means; and
a slide member having a passageway therethrough, said slide member being movably mounted between said first surfaces of said first and second members and sealingly engaged on opposite sides thereof by said first, second, third and fourth sealing means, said slide member being movable between a first position which interrupts communication between said aperture and said opening and a second position in which said passageway establishes communication between said aperture and said opening to permit flow through said valve assembly,
a curette in communication with said aperture; and
air permeable collection means supported within said container by said second member of said valve assembly in communication with said opening for accumulating matter collected by said curette when said slide member is moved to its second position;
wherein first and second sealing means comprise first and second sealing members received in channels provided in said first surface of said first member, and said third and fourth sealing means comprises thrid and fourth sealing members received in channels provided in said first surface of said second member; and wherein a portion of said second sealing member is spaced from a corresponding portion of said first sealing member by a distance greater than the diameter of said passageway through said slide member, and a portion of said fourth sealing member is spaced from a corresponding portion of said third sealing member by a distance greater than the diameter of said passageway, said passageway through said slide member being sealingly located between said respective portions of said first, second, third and fourth sealing members when said slide member is located in its said first position.

2. The self-contained vacuum aspirator of claim 1 wherein said slide member includes limit stop means for establishing said second position with said passageway aligned with said aperture and said opening and for establishing said first position with said passageway located between said respective portions of said first, second, third and fourth sealing members, and further including releasable locking means for maintaining said slide member in its said second position.

3. The self-contained vacuum aspirator of claim 1 wherein a second surface of said second member includes a depending cylindrical portion extending therefrom and in communication with said opening for supporting said collection means.

* * * * *